United States Patent [19]

Zipper

[11] 4,158,050

[45] Jun. 12, 1979

[54] METHOD FOR EFFECTING FEMALE STERILIZATION WITHOUT SURGERY

[75] Inventor: Jaime Zipper, Santiago, Chile

[73] Assignee: International Fertility Research Programme, Research Triangle Park, N.C.

[21] Appl. No.: 915,956

[22] Filed: Jun. 15, 1978

[51] Int. Cl.² ...................... A61K 9/02; A61K 31/435
[52] U.S. Cl. ........................................ 424/14; 424/257
[58] Field of Search ................................. 424/14, 257

[56] References Cited

FOREIGN PATENT DOCUMENTS

| | | |
|---|---|---|
| 2244923 | 4/1974 | Fed. Rep. of Germany. |
| 7212148 | 3/1974 | Netherlands. |
| 7107328 | 8/1972 | South Africa. |
| 1338493 | 11/1973 | United Kingdom. |

OTHER PUBLICATIONS

Chandra et al., Indian J. Exp. Biol. 1974 12(5):447–448, Chemical Occlusion of Rhesus Monkey Oviducts with Quinacrine.

Joseph et al., Amer. J. Obstet. Gynecol. 1974, 119(7): 978–981 Toxic and Antifertility Effects of Quinacrine Hydrochloride in Rats.

Zipper et al., Int. J. Gynaecol. Obstet. 14(6):499–502 (1976), The Clinical Efficacy of the Repeated Transcervical Instillation of Quinacrine for Female Sterilization.

*Primary Examiner*—Shep K. Rose
*Attorney, Agent or Firm*—B. B. Olive

[57] ABSTRACT

The safety and effectiveness of the nonsurgical, female sterilization method involving the inducement of tubal occlusion by the transcervical application of quinacrine hydrochloride is greatly improved when the occluding agent is delivered in the form of a solid pellet.

4 Claims, No Drawings

METHOD FOR EFFECTING FEMALE STERILIZATION WITHOUT SURGERY

BACKGROUND OF THE INVENTION

1. Field of the Invention

The invention relates generally to nonsurgical, female sterilization methods, and more particularly to an improvement in the method for inducing tubal occlusion by the transcervical application of quinacrine hydrochloride.

2. Description of the Prior Art

Demographers have warned that unless effective measures are soon taken to arrest the explosive growth in population, society as a whole faces a future of indescribable bleakness. The seriousness of this problem has been widely recognized and research programs on fertility control have been initiated throughout the world with the principal objective being to develop a safe and effective contraceptive method which is relevant to the conditions of the developing countries, since they contain nearly two-thirds of the world population.

Although the surgical sterilization of women is the most effective method of contraception known, the medical infrastructure required for carrying out such procedures on a mass basis does not exist in the evolving countries. In view of this fact, a high priority has been given to the development of a nonsurgical method for effecting sterilization which can be performed by paramedical personnel and which does not require extensive facilities or equipment.

Previous efforts to achieve this goal have included the infusion of various scarifying and necrotizing agents, tissue glues and tubal plugs into the uterus for the purpose of effecting an occlusion of the gamete carrying oviducts or fallopian tubes. However, these procedures have been abandoned because they are ineffective or are not sufficiently developed to determine their safety or effectiveness.

To date, the only nonsurgical procedure known which appears to have possibilities for effecting the sterilization of women on a mass basis is the transcervical instillation of quinacrine hydrochloride. However, despite the fact that this method offers great promise in fertility control, it has not, prior to the present invention, been sufficiently safe and effective for application on a widespread basis.

Heretofore, the quinacrine hydrochloride has been delivered in the form of a liquid suspension which places limitations on the concentration or dosage level which can be brought into the uterine cavity to achieve maximum effectiveness. Moreover, high fluid pressures often developed within the uterus following injection. The presence of this internal pressure tends to cause excessive uterine distension and carries the risk of leakage into the peritoneal cavity or circulatory system.

Although not a common occurrence, a number of cases of cortical excitation have been reported following the instillation of quinacrine in a liquid carrier. The condition is characterized by nervousness, irritability, emotional change and transient psychosis with the risk that the patient may convulse if not treated promptly. It is believed that the syndrome is due to the rapid intravascular absorption of quinacrine when it is instilled into a highly vascular area.

For a recent clinical evaluation of the procedure just described, reference may be had to a paper titled "The Clinical Efficacy of the Repeated Transcervical Instillation of Quinacrine for Female Sterilization" by J. Zipper, et al., published in Int J Gynaecol Obstet 14:499–502, 1976. The safety and efficacy of the repeated transcervical instillation of quinacrine hydrochloride in a suspension of 2 percent xylocaine was evaluated in 200 patients. All instillation procedures were performed during the proliferative phase of the menstrual cycle. The second instillation was made in the first menstrual cycle following the initial instillation and the third instillation at 6 months after the first. Follow-up visits were scheduled at six month intervals after the last instillation.

The potentially serious complications following the instillation were four cases of cortical excitation and one case of acute adnexitis. Fifty-one pregnancies were reported with forty-one occurring before completion of the three instillations. Based on the results of this study, the authors concluded that it does not appear that the intrauterine instillation of quinacrine hydrochloride is sufficiently effective for widespread use as a nonsurgical sterilization procedure.

It is, therefore, a principal object of this invention to vastly improve the effectiveness of this procedure and to reduce or eliminate the hazards associated with it.

SUMMARY OF THE INVENTION

It has now been found that the method for female sterilization involving the transcervical application of quinacrine hydrochloride to effect occlusion of the utero-tubal junction is greatly improved when the quinacrine compound is delivered in the form of a solid pellet rather than by means of an aqueous suspension as has been the previous practice.

The pelletized quinacrine may be applied alone or with an adjunct such as sodium thiopental, also in pellet form, to enhance the tubal occlusive action and improve intrauterine retention of the quinacrine.

In addition to increasing sterilization rates, administration of the therapeutic agent in the pelletized mode eliminates the hazards of excessive uterine distension and internal pressure which often result when a fluid vehicle is used in the delivery system. Deposition of pellets within the uterus also reduces the risk of rapid intravascular absorption and the resulting side effects, such as cortical excitation, because the uterine cavity is exposed to the quinacrine slowly over a period of ten minutes or more as the pellets dissolve, rather than all at once, as when introduction is made by means of a liquid carrier.

DESCRIPTION OF THE PREFERRED EMBODIMENT

As is known, quinacrine is a derivative of acridine and can be identified chemically as 3-chloro-7-methoxy-9-(1-methyl-4-diethylaminobutylamino) acridine. The compound has a long history of safe use as an antimalarial in hundreds of thousands of individuals. Although quinacrine, per se, may be used in the sterilization procedure of the present invention, it is preferably employed in the form of its hydrochloride salt to provide better solubility.

Since quinacrine hydrochloride is a solid material consisting of bright yellow crystals, it can be readily pelletized by standard procedures. For example, pellets suitable for the purposes of this invention may be formed by adding an inert binding agent and a lubricant to a quantity of quinacrine powder and then compacting the mixture with an arbor press in a cylindrical die.

Water may be used as the binder and magnesium stearate has been found to perform well as a lubricant. Best results are obtained when the binder is present in an amount of about ten percent of the mixture and the lubricant in an amount of about one percent.

The pellets are desirably in the shape of a cylinder with rounded ends. To avoid the need for dilating the cervix during insertion, the pellet diameter should be less than 4 mm. with about 3.5 mm. being preferred. Desirably, the pellets are compacted to contain about 10 mg. of quinacrine per mm. of length with each pellet containing a total of either 250 or 500 mg. Thus, since the usual dosage for each instillation is 500 mg., this can be delivered with one pellet or if smaller pellets are desired two pellets may be used to provide the desired quantity. However, since dosage levels are subject to variation, the amount of quinacrine carried by each pellet may be altered accordingly.

The pellet or pellets are deposited in the uterine cavity by utilizing well-known insertion techniques. For example, proper instillation can be accomplished by a procedure which involves first placing the pelletized material in a plastic tube with a push rod being positioned behind the pellets. The tube is then passed through the cervical canal and inner ostium until the fundus is reached. At this point, the push rod is held stationary and the tube is pulled back over it to expel the pellets into the uterine cavity. After the pellets have been discharged, the insertion device is, of course, removed.

Although not an essential requirement of the invention, from about 15 to 25 mg. and preferably 20 mg. of sodium thiopental may be used as an adjunct to improve the intrauterine retention of the quinacrine pellets. Since sodium thiopental is a hygroscopic substance, it causes an increase in the viscosity of the uterine fluid which tends to make expulsion of the quinacrine pellets less likely. When used, the sodium thiopental is deposited in the uterine cavity simultaneously with the quinacrine pellets and likewise in pellet form.

The safety and efficacy of the procedure according to the present invention was evaluated on a continuing basis involving initially 139 patients who entered the program over various periods of time. The completed program involved three instillations roughly at one month intervals corresponding with the menstrual cycle for each patient. A first follow-up was made six months after the third instillation and a second follow-up was carried out after a twelve month period had expired after the last instillation.

The results obtained are reported in tabular form in the following tables:

TABLE I

|  | Women Receiving Insertion | Cases After No. | Closed Insertion % | Reasons For Closing Case |
|---|---|---|---|---|
| Insertion I | 139 | 5 | 3.6 | Patient choice(2) ovarian cyst(1) lost to follow-up(2)* |
| Insertion II | 131 | 4 | 3.1 | Mild sinequia(1) investigator's choice(1) pelvic/abdominal pain(1) lost to follow-up(1) |
| Insertion III | 116 | 1 | 0.9 | Pregnancy(1) |

*One patient who did not return for the second insertion became pregnant.

TABLE II

| DIFFICULTY WITH INSERTIONS | | | | | | | | |
|---|---|---|---|---|---|---|---|---|
|  | Insertion No. I (N=139)* | | Insertion No. II (N=131)* | | Insertion No. III (N=116)* | | Total Insertions (N=386) | |
|  | No. | % | No. | % | No. | % | No. | % |
| Hard pellet | 0 | 0.0 | 0 | 0.0 | 1 | 0.9 | 1 | 0.3 |
| Unable to release pellet | 2 | 1.4 | 1 | 0.8 | 2 | 1.7 | 5 | 1.3 |
| Patient expelled pellet | 0 | 0.0 | 1 | 0.8 | 1 | 0.9 | 2 | 0.5 |
| Mild sinequia | 0 | 0.0 | 1 | 0.8 | 1 | 0.9 | 2 | 0.5 |
| TOTAL | 2 | 1.4 | 3 | 2.3 | 5 | 4.3 | 10 | 2.6 |

*Number of patients

TABLE III

| Complication Complaints at Time of Insertion | | | | | | |
|---|---|---|---|---|---|---|
|  | Insertion No. I (N=139)* | | Insertion No. II (N=131)* | | Insertion No. III (N=116)* | |
|  | No. | % | No. | % | No. | % |
| Mild pelvic/abdominal pain | 4 | 2.9 | 5 | 3.8 | 2 | 1.7 |

*Number of patients

TABLE IV

| Complications/Complaints between Insertions | | | | | | | | |
|---|---|---|---|---|---|---|---|---|
|  | Insertions I - II (N=131)* | | Insertions II - III (N=116)* | | Insertion III - ** (N=70)* | | Follow-up ** _ *** (N=14)* | |
|  | No. | % | No. | % | No. | % | No. | % |
| Dizziness | 1 | 0.8 | 9 | 0.0 | 0 | 0.0 | 0 | 0.0 |
| Dizziness, pain, contractions | 1 | 0.8 | 0 | 0.0 | 0 | 0.0 | 0 | 0.0 |
| Pelvic/abdominal pain | 5 | 3.8 | 9 | 7.9 | 0 | 0.0 | 0 | 0.0 |
| Amenorrhea | 2 | 1.5 | 1 | 0.9 | 0 | 0.0 | 0 | 0.0 |

TABLE IV-continued

| | Complications/Complaints between Insertions | | | | | | |
|---|---|---|---|---|---|---|---|
| | Insertions I - II (N=131)* | | Insertions II - III (N=116)* | | Insertion III - ** (N=70)* | | Follow-up ** - *** (N=14)* |
| | No. | % | No. | % | No. | % | No. % |
| Chemical discharge | 1 | 0.8 | 0 | 0.0 | 0 | 0.0 | 0 0.0 |
| Delayed menses | 1 | 0.8 | 0 | 0.0 | 0 | 0.0 | 0 0.0 |
| Ovarian cyst | 1 | 0.8 | 0 | 0.0 | 0 | 0.0 | 0 0.0 |
| Intense vaginitis | 1 | 0.8 | 0 | 0.0 | 0 | 0.0 | 0 0.0 |
| Intense pain | 1 | 0.8 | 0 | 0.0 | 0 | 0.0 | 0 0.0 |
| Dysmenorrhea | 0 | 0.0 | 0 | 0.0 | 0 | 0.0 | 0 0.0 |
| Pregnancy | 0 | 0.0 | 0 | 0.0 | 1 | 1.4 | 0 0.0 |
| Severe headache | 0 | 0.0 | 0 | 0.0 | 0 | 0.0 | 1 7.1 |
| TOTAL | 14 | 10.7 | 10 | 8.7 | 1 | 1.4 | 2 14.2 |

*Number of patients
**6 month follow-up
***12 month follow-up

Attention is directed to the fact that only one pregnancy is reported in Table IV above. This is a dramatic improvement over the results obtained in an evaluation of the method as previously practiced in the Zipper, et al paper previously referred to where a 25.5% pregnancy rate was reported as having occured.

It is apparent that the prospects of chemical sterilization with quinacrine having a substantial demographic impact in the future are greatly enhanced by the improved means of delivery provided by the present invention.

What is claimed is:

1. In a nonsurgical method for female sterilization wherein a liquid suspension of quinacrine hydrochloride is introduced into the uterine cavity in one or more treatments to effect an occlusion of the utero-tubal junction, the improvement which comprises applying said quinacrine hydrochloride in the form of a solid pellet having the configuration of a cylinder with rounded heads, a diameter of less than 4 millimeters and containing about 10 mg. of quinacrine hydrochloride per millimeter of length.

2. The improved method of claim 1 wherein said solid pellet contains 250 mg. of quinacrine hydrochloride and two pellets are administered with each treatment.

3. In a nonsurgical method for female sterilization wherein a liquid suspension of quinacrine hydrochloride is introduced into the uterine cavity in one or more treatments to effect an occlusion of the utero-tubal junction, the improvement which comprises applying said quinacrine hydrochloride in combination with sodium thiopental with both of said compounds being in the form of a solid pellet having the configuration of a cylinder with rounded heads, a diameter of less than 4 millimeters and containing about 10 mg. of quinacrine hydrochloride per millimeter of length.

4. The improved method according to claim 3 wherein said quinacrine hydrochloride is applied at a dosage level of 500 mg. in each treatment and said sodium thiopental is applied at a dosage in the range of from 15 to 25 mg.

* * * * *

UNITED STATES PATENT AND TRADEMARK OFFICE
CERTIFICATE OF CORRECTION

PATENT NO. : 4,158,050
DATED : June 12, 1979
INVENTOR(S) : Jaime Zipper

It is certified that error appears in the above-identified patent and that said Letters Patent are hereby corrected as shown below:

In Col. 4, Table III, Insert a slant mark between "Complication" and "Complaints".

In Col. 4, Table IV, In line entitled "Dizziness" the number "9" should read --0--.

In Col. 5, Table IV, continued, In the line entitled "Dysmenorrhea" the last "0" and "0.0" should read --1-- and --7.1--, respectively.

Signed and Sealed this

Sixth Day of November 1979

[SEAL]

Attest:

RUTH C. MASON
Attesting Officer

LUTRELLE F. PARKER
Acting Commissioner of Patents and Trademarks